(12) United States Patent
Justis et al.

(10) Patent No.: US 6,210,413 B1
(45) Date of Patent: Apr. 3, 2001

(54) CONNECTING APPARATUS USING SHAPE-MEMORY TECHNOLOGY

(75) Inventors: Jeff R. Justis, Cordova; Michael C. Sherman, Memphis, both of TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/408,364

(22) Filed: Sep. 29, 1999

Related U.S. Application Data
(60) Provisional application No. 60/130,911, filed on Apr. 23, 1999.

(51) Int. Cl.$^7$ ............................. A61B 17/70; A61B 17/68
(52) U.S. Cl. ................................. 606/61; 606/60
(58) Field of Search ................. 606/60, 61, 72, 606/73

(56) References Cited

U.S. PATENT DOCUMENTS

| | | | |
|---|---|---|---|
| 5,562,663 | * 10/1996 | Wisnewski et al. | 606/61 |
| 5,669,910 | * 9/1997 | Korhonen et al. | 606/61 |
| 5,702,393 | * 12/1997 | Pfaifer | 606/61 |
| 5,709,685 | * 1/1998 | Dombrowski et al. | 606/61 |
| 5,785,711 | * 7/1998 | Errico et al. | 606/61 |
| 5,814,046 | * 9/1998 | Hopf | 606/61 |
| 5,873,878 | * 2/1999 | Harms et al. | 606/61 |
| 5,989,250 | * 11/1999 | Wagner et al. | 606/61 |
| 6,001,098 | * 12/1999 | Metz-Stavenhagen et al. | 606/61 |
| 6,080,156 | * 6/2000 | Asher et al. | 606/61 |
| 6,110,173 | * 8/2000 | Thomas, Jr. | 606/61 |
| 6,123,706 | * 9/2000 | Lange | 606/61 |
| 6,132,432 | * 10/2000 | Richelsoph | 606/61 |

* cited by examiner

*Primary Examiner*—Gene Mancene
*Assistant Examiner*—Michael B. Priddy
(74) *Attorney, Agent, or Firm*—Woodard, Emhardt, Naughton, Moriarty & McNett

(57) ABSTRACT

An apparatus for connecting two members uses shape-memory technology. The connecting apparatus includes a first module having a connector portion adapted for connection to a first member, and a second module having a connector portion adapted for connection to a second member. Each module has a pair of flanges extending therefrom which are disposed about and overlap a portion of the connector portion of the other module. In one embodiment, a compression member at least partially formed of a shape-memory material is disposed adjacent to the flanges and has a first configuration at one temperature which allows relative movement between the modules, and a second configuration at a different temperature which limits relative movement between the modules. In another embodiment, each pair of flanges is at least partially formed of a shape-memory material and has a first configuration at one temperature which allows relative movement between the modules, and a second configuration at a different temperature which limits relative movement between the modules.

36 Claims, 5 Drawing Sheets

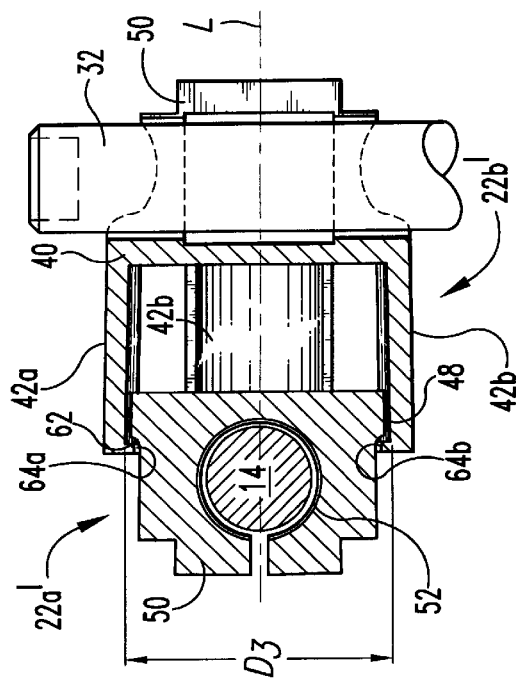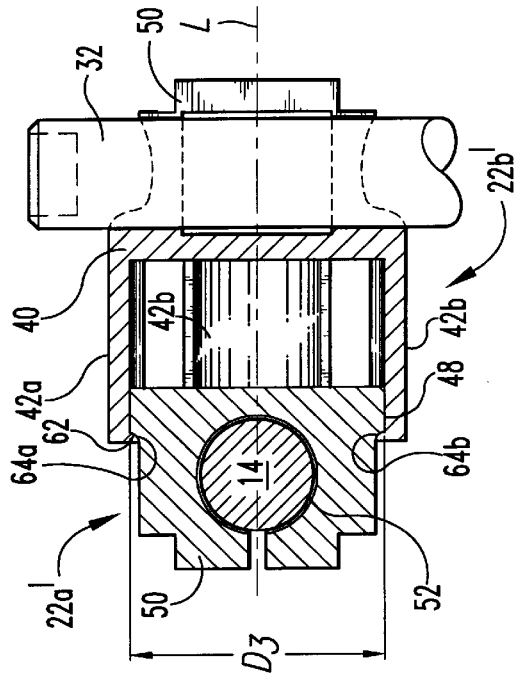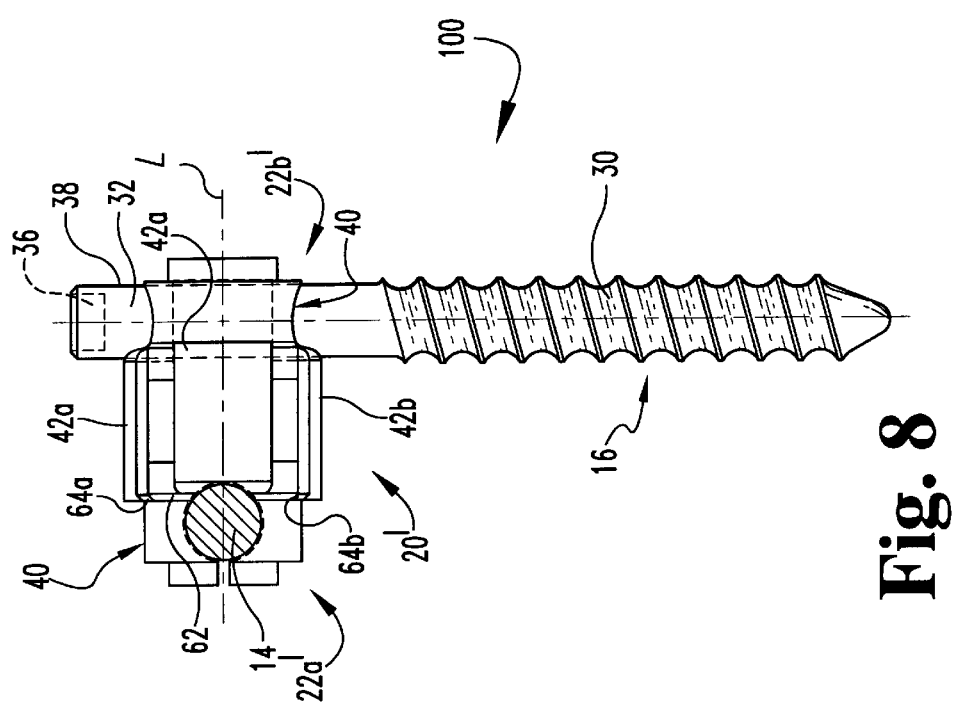

CONNECTING APPARATUS USING SHAPE-MEMORY TECHNOLOGY

This application is based on provisional patent application Serial No. 60/130,911, filed Apr. 23, 1999, and priority is claimed in the present application to the extent the subject matter of this application is found in that provisional application. The content of that application is incorporated herein by reference.

FIELD OF THE INVENTION

The present invention broadly concerns an apparatus for connecting two or more members using shape-memory technology. Specifically, but not exclusively, the invention concerns an apparatus for connecting a spinal rod and a bone anchor for use in a spinal fixation system.

BACKGROUND OF THE INVENTION

Several techniques and systems have been developed for correcting and stabilizing the spine and for facilitating fusion at various levels of the spine. In one type of system, a bendable rod is disposed longitudinally along the length of the spine or vertebral column. The rod is preferably bent to correspond to the normal curvature of the spine in the particular region being instrumented. For example, the rod can be bent to form a normal kyphotic curvature for the thoracic region of the spine, or a lordotic curvature for the lumbar region. In accordance with such a system, the rod is engaged to various vertebrae along the length of the spinal column by way of a number of fixation elements. A variety of fixation elements can be provided which are configured to engage specific portions of the vertebra. For instance, one such fixation element is a hook that is configured to engage the laminae of the vertebra. Other prevalent fixation elements include spinal screws or bolts, which can be threaded into various portions of vertebral bone.

In one typical procedure utilizing a bendable spinal rod, the rod is situated on opposite sides of the spine or spinous processes. A plurality of fixation elements is attached to a portion of several vertebral bodies. The rods are then affixed to the plurality of fixation elements to apply corrective and stabilizing forces to the spine.

One example of a rod-type spinal fixation system is the TSRH® Spinal System sold by Danek Medical, Inc. The TSRH® System includes elongated rods and a variety of hooks, screws and bolts, all configured to create a segmental construct throughout the spine. In one aspect of the TSRH® System, the spinal rod is connected to the various vertebral fixation elements by way of an eyebolt. In this configuration, the fixation elements are engaged to the spinal rod laterally adjacent to the rod. In another aspect of the TSRH® System, a variable-angle screw is engaged to the spinal rod by way of an eyebolt. The variable-angle screw allows pivoting of the bone screw in a single plane parallel to the plane of the spinal rod. Details of this variable angle screw can be found in U.S. Pat. No. 5,261,909 to Sutterlin et al., owned by the Assignee of the present invention. One goal achieved by the TSRH® System is that the surgeon can apply vertebral fixation elements, such as spinal hooks or bone screws, to the spine in appropriate anatomic positions. The TSRH® System also allows the surgeon to easily engage a bent spinal rod to each of the fixation elements for final tightening.

In recent years, a special material known as "shape-memory alloy" has been used in the construction of various mechanical devices. This type of material is an alloy of known metals, such as copper and zinc, nickel and titanium, silver and cadmium, and others, that are known to exhibit a "shape-memory" in which a particular component formed of a shape-memory alloy (SMA) is capable of reforming to a "memorized" shape at certain temperatures. This shape-memory characteristic occurs when the SMA alloy changes from a martensitic crystal phase to an austenitic crystal phase. In the martensite stage, the SMA is relatively weak and pliable. As the temperature of the SMA component is increased above its transformation temperature range, the SMA transforms to an austenitic stage and the material becomes relatively strong with super-elastic properties. Generally, the strength and super-elastic characteristics of a shape-memory material tend to increase toward the high temperature end of the transformation temperature range and decrease toward the low temperature end. While there are many alloys that exhibit shape-memory characteristics, one of the more common SMAs is an alloy of nickel and titanium. One such well known alloy is Nitinol®, which has proven to be highly effective for devices to be placed within the human body because its transformation temperature range falls between room temperature and normal human body temperature.

In rod-type spinal fixation systems of the past, set screws typically have been used to fix the location and orientation of hooks or spinal screws along the length of a spinal rod. However, the set screws have been known to have a tendency to back out in in-vivo situations. This could likely cause the device to loosen, thus requiring additional surgery. Moreover, the set screws may strip or gall and their installation can be cumbersome because of the limited amount of room available to manipulate the tools necessary to drive the set screws into their engaged position. There is therefore a need to provide a connecting apparatus, which eliminates reliance on set screws, or other similar devices to affix hooks, bolts or spinal screws to a spinal rod. This need also encompasses a goal of minimizing the profile and bulk of the components used to connect the hooks, bolts or screws to the spinal column. Moreover, it is desirable to reduce the number of components that must be manipulated by the surgeon during a surgical procedure.

While prior attempts have been made to remedy the above-mentioned shortcomings of prior rod-type spinal fixation systems, there is a need remaining in the industry for an improved connecting apparatus that engages and connects two members using shape-memory technology. The present invention meets this need and provides other benefits and advantages in a novel and unobvious manner.

SUMMARY OF THE INVENTION

The present invention relates to a connecting apparatus for connecting two or more members using shape-memory technology. While the actual nature of the invention covered herein can only be determined with reference to the claims appended hereto, certain forms of the invention that are characteristic of the preferred embodiments disclosed herein are described briefly as follows.

In each form of the present invention, a connecting apparatus includes a first module having a connector portion adapted for connection to a first member, and a second module having a connector portion adapted for connection to a second member. Additionally, each form of the present invention utilizes shape-memory technology to connect the first member to the second member.

In one form of the present invention, each module has a flange extending therefrom, which is disposed adjacent to and overlaps a portion of the connector portion of the other module. A compression member at least partially formed of a shape-memory material is disposed adjacent to the flanges and has a first configuration at one temperature which allows relative movement between the modules, and a second configuration at a different temperature which limits relative movement between the modules.

In another form of the present invention, each module has a pair of flanges extending therefrom, wherein at least one flange of each pair of flanges is at least partially formed of a shape-memory material. Each pair of flanges is disposed adjacent to and overlaps a portion of the connector portion of the other module. Each pair of flanges has a first configuration at one temperature, which allows relative movement between the modules, and a second configuration at a different temperature which limits relative movement between the modules.

In a further form of the present invention, each module has a fixation portion extending therefrom which is disposed adjacent to and overlaps a portion of the connector portion of the other module. Further included is shape-memory means which allows relative movement between the modules at one temperature and limits relative movement between the modules at a different temperature.

In an additional form of the present invention, only one of the modules has a pair of flanges extending therefrom. The pair of flanges is disposed adjacent to and overlaps a portion of the connector portion of the other module. A compression member at least partially formed of a shape-memory material is disposed about at least a portion of the flanges and has a first configuration at one temperature which allows relative movement between the modules, and a second configuration at a different temperature which limits relative movement between the modules. Further included is a locking member at least partially formed of a shape-memory material, and wherein at least one of the connector portions includes a clamping section. The locking member is disposed about at least a portion of the clamping section and allows relative movement between the clamping section and the corresponding one of the first and second members when at one temperature, while limiting relative movement between the clamping section and the corresponding one of the first and second members when at a different temperature.

In yet another form of the present invention, only one of the modules has a pair of flanges extending therefrom. At least one flange is at least partially formed of a shape-memory material. The pair of flanges is disposed adjacent to and overlaps a portion of the connector portion of the other module and has a first configuration at one temperature which allows relative movement between the modules, and a second configuration at a different temperature which limits relative movement between the modules. At least one of the connector portions includes a clamping section at least partially formed of a shape-memory material. The clamping section allows relative movement between the clamping section and the corresponding one of the first and second members at one temperature, and limits relative movement between the clamping section and the corresponding one of the first and second members at a different temperature.

Other forms of the present invention include incorporating a lip onto one of the modules and a shoulder onto the other of the modules. The lip and shoulder cooperate to provisionally maintain the first and second modules in a telescopic relationship.

It is one object of the present invention to provide a connecting apparatus for connecting two or more members using shape-memory technology.

Another object of the present invention is to provide a connecting apparatus for use in a spinal fixation system for connecting a spinal rod to a plurality of bone anchors.

Still another object of the present invention is to provide a connecting apparatus that can engage and connect two members while allowing the members to translate relative to one another during an unsecured state.

Further objects, features, advantages, benefits, and aspects of the present invention will become apparent from the drawings and description contained herein.

BRIEF DESCRIPTION OF THE DRAWINGS

FIG. 8 is a side elevation view of a spinal fixation system connecting apparatus according to another embodiment of the present invention.

FIG. 9 is a cross-sectional view of the connecting apparatus depicted in FIG. 8 illustrating a first operational configuration of the connecting apparatus.

FIG. 10 is a cross-sectional view of the connecting apparatus depicted in FIG. 8 illustrating a second operational configuration of the connecting apparatus.

DESCRIPTION OF THE PREFERRED EMBODIMENTS

Figure 1:
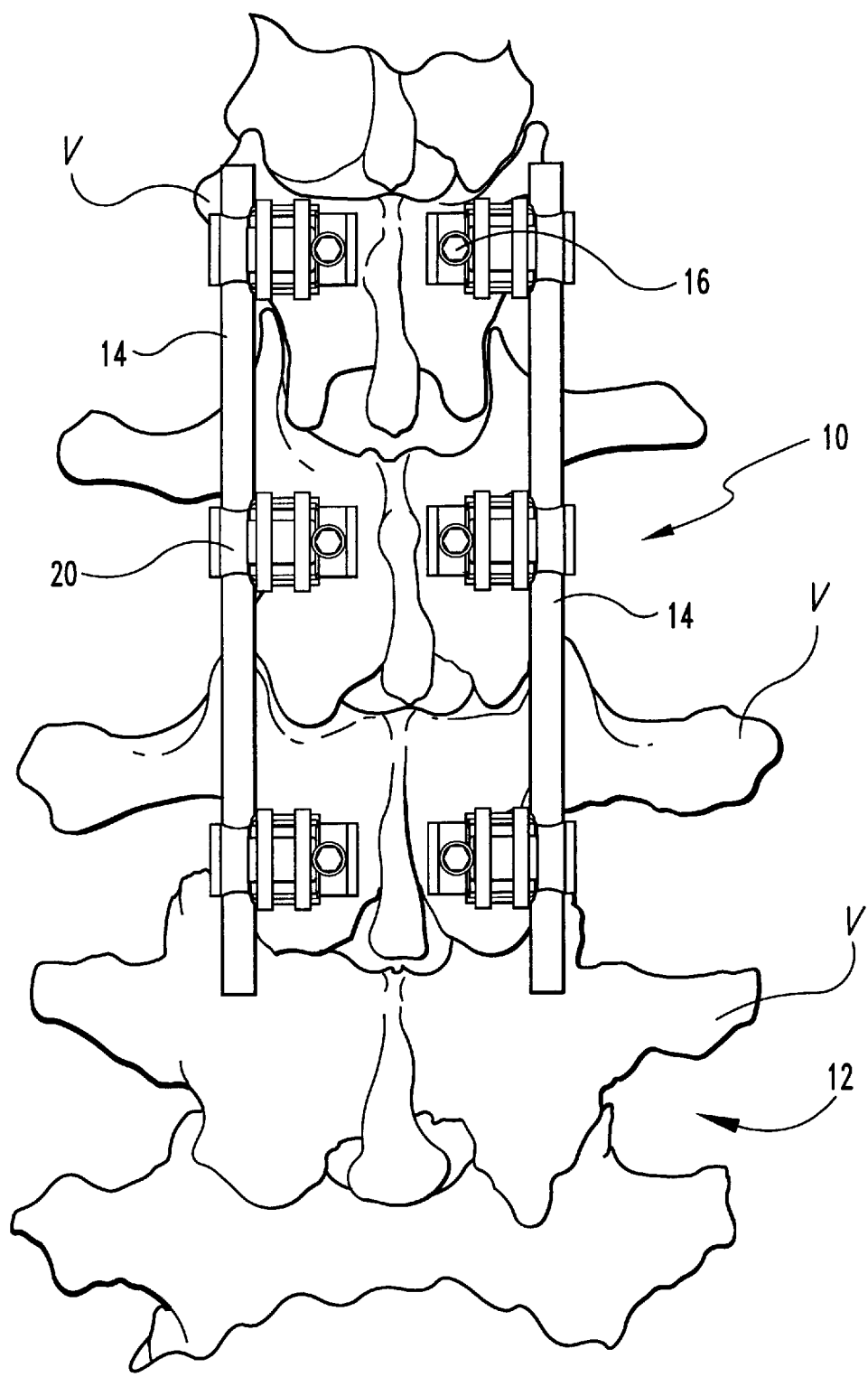
FIG. 1 is a posterior view of a vertebral column showing a spinal fixation system according to an embodiment of the present invention attached thereto.

For the purposes of promoting an understanding of the principles of the invention, reference will now be made to the embodiment illustrated in the drawings and specific language will be used to describe the same. It will nevertheless be understood that no limitation of the scope of the invention is thereby intended, any alterations and further modifications in the illustrated device, and any further applications of the principles of the invention as illustrated therein being contemplated as would normally occur to one skilled in the art to which the invention relates.

FIG. 1 depicts a spinal fixation system 10 according to one embodiment of the present invention. System 10 is shown attached to a vertebral column 12 comprised of a plurality of vertebra V. System 10 generally includes a pair of spinal rods 14, situated on opposite sides of spinal column 12, and a plurality of bone anchors 16, each attached to a portion of vertebra V and affixed along the length of spinal rods 14. Although the instrumentation of three vertebrae are shown, it should be understood that system 10 can vary in size and configuration such that any number of vertebra V can be held in place relative to one another. It should further be understood that, although it is preferable to attach a spinal rod 14 to each side of spinal column 12, system 10 can include a single spinal rod 14 attached to one side of spinal column 12. Additionally, system 10 can be used in a variety of applications associated with the spine to address a wide range of spinal pathologies. For example, application of system 10 can be limited to the lumbar region of the spine for fixation following a diskectomy. Alternatively, system 10 can extend substantially along the entire length of the thoracic and lumbar regions of the spine to correct a deformity such as scoliosis. In other applications, system 10 can provide fixation and stabilization of the cervical spine, such as might occur following a fracture or dislocation. It is of course understood by a person of skill in the art that the configuration of the components of system 10 will vary depending upon the region of the spine to be treated and the type of treatment to be administered.

Figure 2:
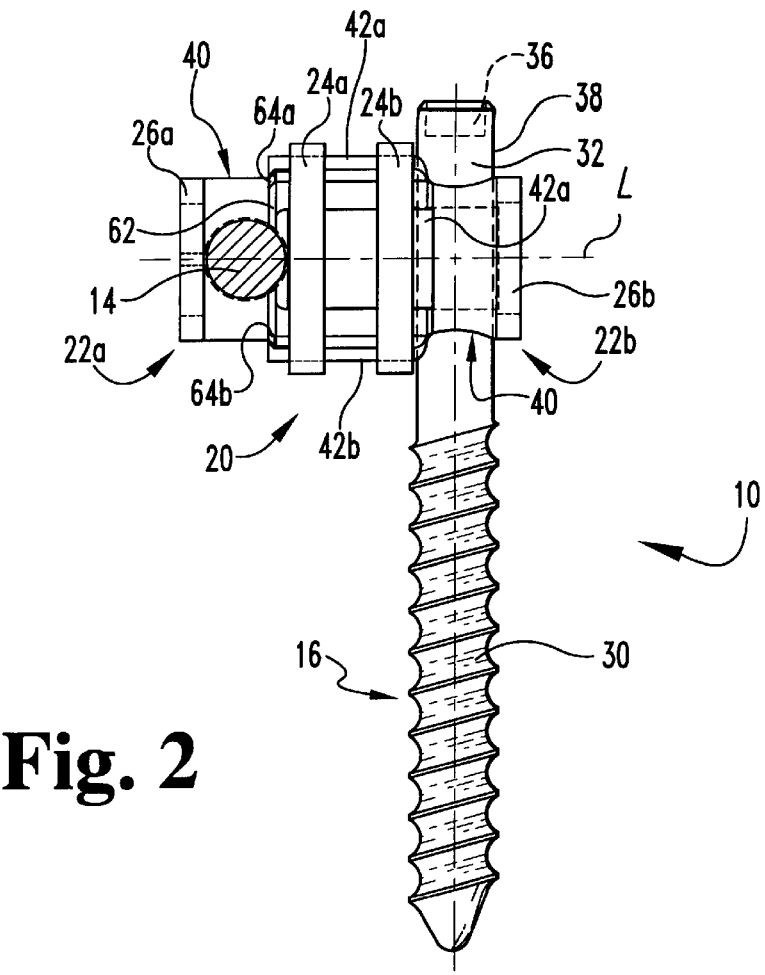
FIG. 2 is an enlarged view of one connecting apparatus of the system depicted in FIG. 1.
Figure 3:
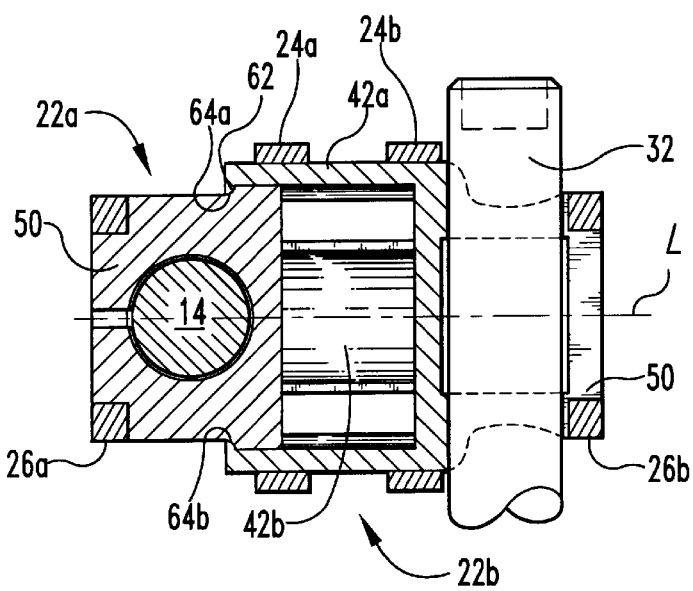
FIG. 3 is a cross-sectional view of the connecting apparatus depicted in FIG. 2.
Figure 4:
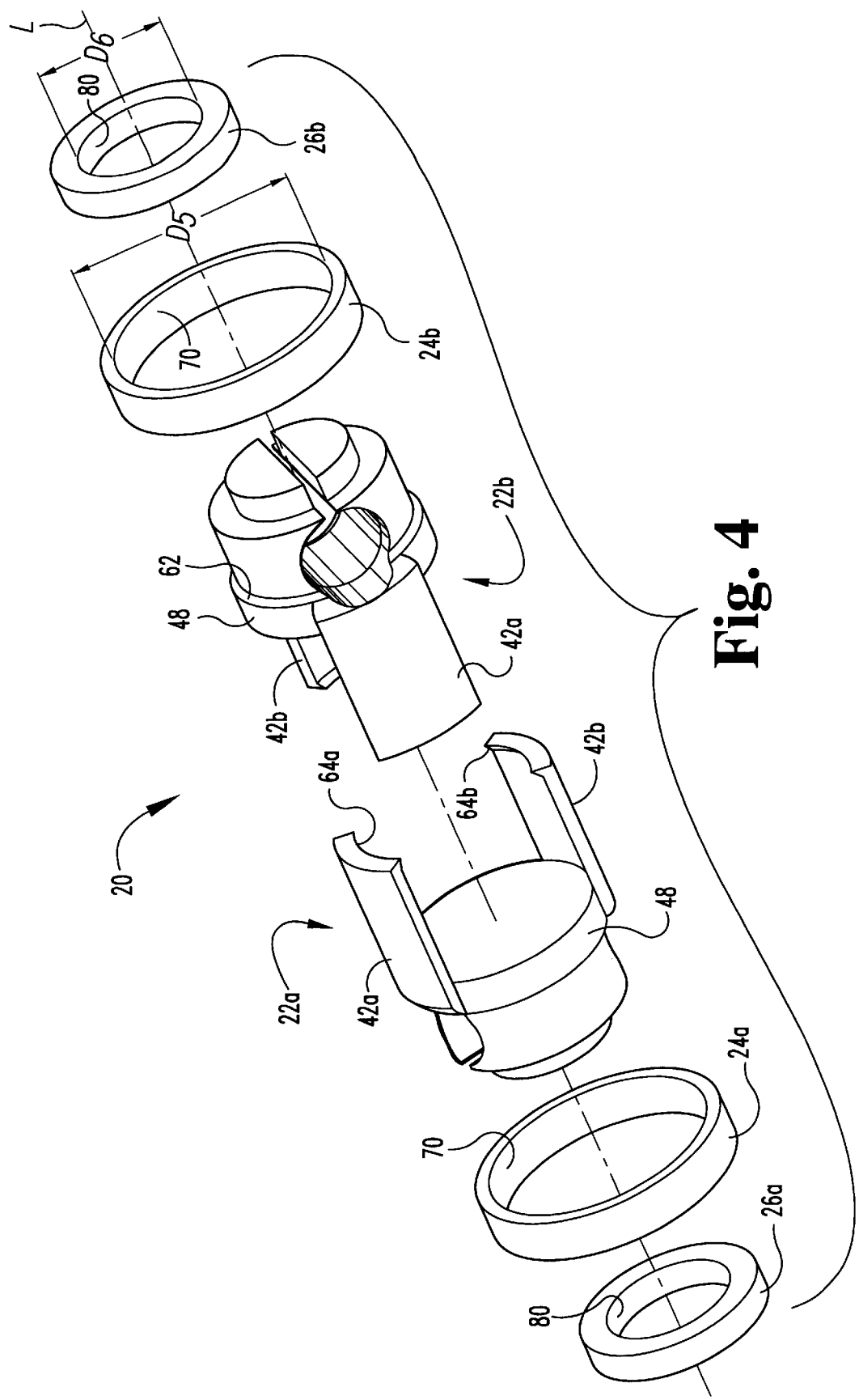
FIG. 4 is an exploded perspective view of one embodiment of a connecting apparatus for use with the system depicted in FIG. 1.

FIGS. 2–4 provide additional details concerning the structure and operation of system 10. As shown in FIGS. 2–3, bone anchor 16 is connected to spinal rod 14 by way of a connecting apparatus 20. As most clearly shown in FIG. 4, connecting apparatus 20 includes first and second modules 22a, 22b, first and second compression members 24a, 24b and first and second locking members 26a, 26b. Connecting apparatus 20 also defines a longitudinal axis L.

Referring specifically to FIG. 2, bone anchor 16 includes a threaded shank 30 that carries threads configured to engage bone. In one specific embodiment, the threads are cancellous threads configured to engage vertebral bone, such as vertebra V. Bone anchor 16 also includes an upper portion 32. Upper portion 32 preferably, but not necessarily, includes a tool receiving recess 36. Tool receiving recess 36 can be configured to accept any type of known driving tool. In a specific embodiment, tool receiving recess 36 is a hex recess sized to receive the hex end of a driving tool to allow for the threading of bone anchor 16 into a portion of vertebra V. Upper portion 32 defines a generally circular outer surface 38. It should be understood, however, that outer surface 38 can take on a variety of shapes, such as a square, an ellipse, or a number of other polygonal configurations. Similarly, although spinal rod 14 is shown as having a generally circular cross-section, it should be understood that spinal rod 14 can also take on a variety of alternative shapes and configurations.

Figure 5:
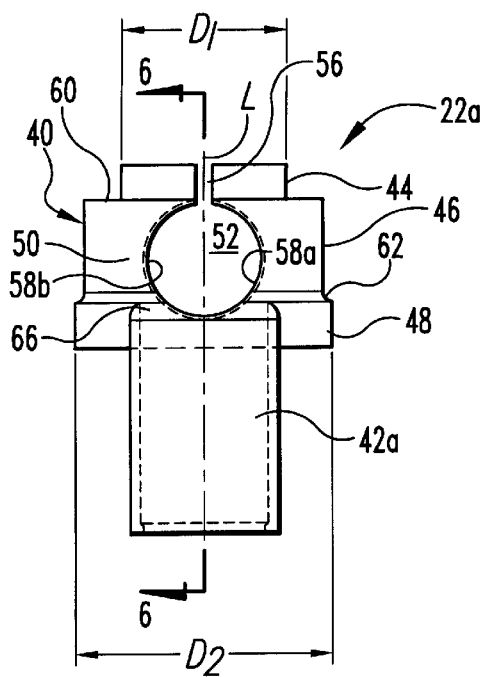
FIG. 5 is a side elevation view of a connecting module for use with the connecting apparatus depicted in FIG. 4.
Figure 6:
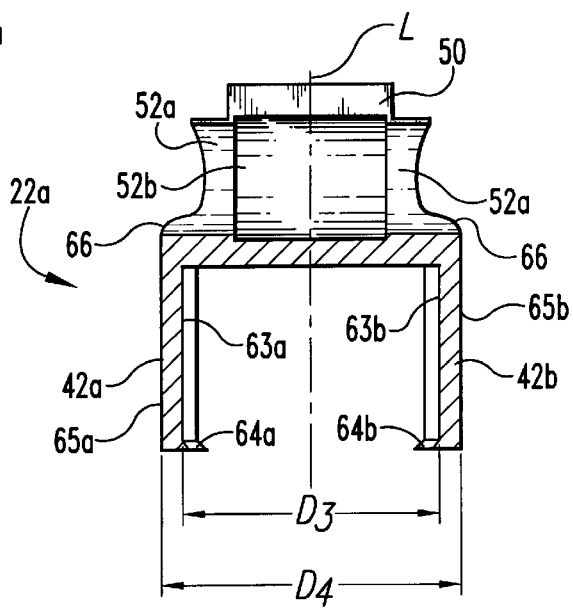
FIG. 6 is a cross-sectional view of the connecting module depicted in FIG. 5 taken along line 6—6 of FIG. 5.
Figure 7:
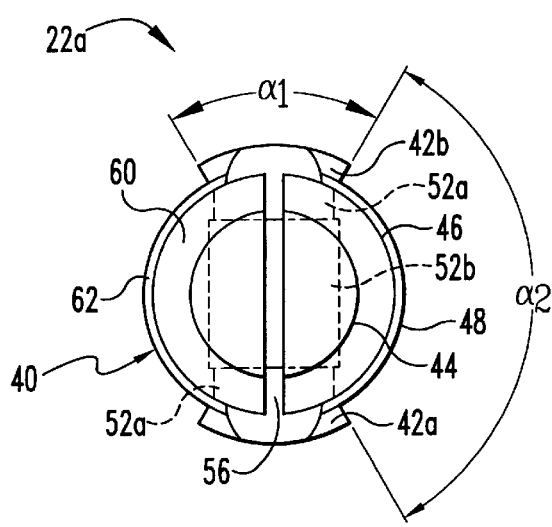
FIG. 7 is a top view of the connecting module depicted in FIG. 5.

Referring now to FIGS. 5–7, shown therein are various structural details of first module 22a. Because first and second modules 22a, 22b have substantially identical configurations, for simplicity, FIGS. 5–7 refer only to the configuration of first module 22a. However, it should be understood that modules 22a, 22b may take on different configurations depending upon the particular application. First module 22a includes a connector portion 40 and a pair of generally opposing flanges 42a, 42b extending therefrom and aligned generally parallel with longitudinal axis L. Connector portion 40 has a substantially circular shape and includes an upper portion 44, an intermediate portion 46 and a lower portion 48. Connector portion 40 defines a clamping section 50, at least partially defined by upper portion 44 and intermediate portion 46.

Clamping section 50 defines an opening 52 extending therethrough and aligned generally perpendicular to longitudinal axis L. In one specific embodiment, opening 52 has a first cross-sectional area 52a and a second cross-sectional area 52b, as shown most clearly in FIG. 6. In this specific embodiment, first cross-sectional area 52a has a diameter that is substantially equal to either the diameter of spinal rod 14 or upper portion 32 of bone anchor 16. Second cross-sectional area 52b has a diameter that is somewhat larger than the diameter of first cross-sectional area 52a, the advantage of which will be discussed later. It should be understood, however, that opening 52 can be configured to define a single, uniform cross-sectional area. Clamping section 50 also defines a slit 56 intersecting opening 52. Slit 56 extends through upper portion 44 and through a portion of intermediate portion 46. In a preferred embodiment, slit 56 extends across the entire width of intermediate portion 46 and is aligned generally along longitudinal axis L. Opening 52 and slit 56 thus cooperate to define a C-shaped recess bounded by a pair of generally opposing sidewalls 58a, 58b. It should be understood that opening 52 and slit 56 may define alternatively shaped recesses as well. For example, a U-shaped recess is also contemplated.

Upper portion 44 has a diameter $D_1$. The diameter of intermediate portion 46 is greater than diameter $D_1$, thus defining an annular shoulder 60 extending continuously about connector portion 40. Lower portion 48 has a diameter $D_2$ that is slightly greater than the diameter of intermediate portion 46, thus defining annular shoulder 62 extending continuously about connector portion 40. Annular shoulder 62 is preferably inwardly rounded to define a circular fillet. However, it should be understood that annular shoulder 62 can take on other configurations, such as an angled transition between upper portion 46 and lower portion 48.

Opposing flanges 42a, 42b generally define a partial cylinder and are disposed generally about longitudinal axis L. Flanges 42a, 42b are positioned on opposite sides of connector portion 40 and define an inner diameter $D_3$ between inner surface 63a of flange 42a and inner surface 63b of flange 42b. Flanges 42a, 42b also define an outer diameter $D_4$ between outer surface 65a of flange 42a and outer surface 65b of flange 42b. Inner diameter $D_3$ is substantially equal to diameter $D_2$ of lower portion 48. Flanges 42a, 42b preferably, but not necessarily, define an inwardly extending lip 64a, 64b. Lips 64a, 64b have a partially circular shape, thus defining a circular round which generally corresponds to the circular fillet defined by annular shoulder 62. It should be understood that lips 64a, 64b can also take on other configurations, such as having an angled surface which generally corresponds to an angled transition between upper portion 46 and lower portion 48. The ends of flanges 42a, 42b which are positioned adjacent connector portion 40 preferably define a rounded end portion 66 to eliminate sharp edges which may be detrimental during the installation of system 10. As shown in FIG. 7, each of flanges 42a, 42b extends across an angle $\alpha_1$ and are separated from one another by an angle $\alpha_2$. In one specific embodiment, angle $\alpha_1$ is about 60° and angle $\alpha_2$ is about 120°. However, it should be understood that these angles are exemplary and are not intended to limit the scope of protection in any manner.

Although first module 22a is illustrated in FIGS. 5–7 as having a pair of generally opposing flanges 42a, 42b, in another embodiment of connecting apparatus 20, first module 22a and second module 22b can each have a single flange extending therefrom. In yet another embodiment, one of modules 22a, 22b can include a pair of flanges 42a, 42b, while the other of the modules includes either a single flange or no flanges. In a specific embodiment, flanges 42a, 42b are attached to connector portion 40, for example, by welding. However, it should be understood that flanges 42a, 42b may also be formed as an integral part of connector portion 40.

Referring back to FIGS. 2–3, it can be seen that first and second compression members 24a, 24b are disposed about a portion of first and second modules 22a, 22b. More specifically, compression members 24a, 24b are disposed along longitudinal axis L and about a portion of flanges 42a, 42b of modules 22a, 22b. In one feature of the present invention, each of compression members 24a, 24b has a substantially similar configuration. However, it is also contemplated that compression members 24a, 24b may take on different configurations depending on the particular application. Additionally, although the specific embodiment of connecting apparatus 20 is shown to include two compression members 24a, 24b, it should be understood that connecting apparatus 20 need possess only a single compression member.

Compression members 24a, 24b are at least partially formed of a shape-memory material such as, for example, Nitinol®, a biocompatible shape-memory metal alloy of nickel and titanium. It is well known in the art that articles made of such shape-memory materials are pliable and can typically be readily reshaped at temperatures below their transformation temperature range. Such articles can be trained to have a pre-programmed shape which the article will change into when the material reaches a temperature above its transformation temperature range. Thus, after being deformed from its original state, the article will attempt to return to its pre-programmed shape when heated up to a temperature above its transformation temperature range. In so doing, the article converts heat energy into mechanical work. There is a wide variety of shape-memory materials, including shape-memory metal alloys (e.g., titanium based alloys and iron based alloys) and shape-memory polymers, which have a wide range of possible transformation temperature ranges. Selection of an appropriate shape-memory material will depend, in large part, on the required material properties for the particular application and the working environment of the device. Nitinol® is well suited for the particular application of the present invention because it provides a transformation temperature range between room temperature and normal human body temperature. Moreover, Nitinol® has a very low corrosion rate, which provides an advantage when used within the human body. Additionally, implant studies in animals have shown minimal elevations of nickel in the tissues in contact with the Nitinol® material. However, it should be understood that other medical-grade shape-memory materials could alternatively be used in place of Nitinol®.

As is most clearly seen in FIG. 4, compression members 24a, 24b are generally ring-shaped and define an inner diameter $D_5$. It should be understood that while compression members 24a, 24b are depicted as circular rings, other shapes and configurations are also contemplated as would occur to one of ordinary skill in the art. When the shape-memory material is in its martensitic or room temperature state, inner diameter $D_5$ is slightly greater than outer diameter $D_4$ of flanges 42a, 42b. In other words, each of compression members 24a, 24b includes an inner surface 70 that generally corresponds to outer surfaces 65a, 65b of flanges 42a, 42b, such that compression members 24a, 24b can be slidably received over flanges 42a, 42b of first and second modules 22a, 22b when the shape-memory material is at a temperature below its transformation temperature range.

Referring again to FIGS. 2–3, it can be seen that first and second locking members 26a, 26b are disposed about a portion of first and second modules 22a, 22b. More specifically, locking members 26a, 26b are disposed along longitudinal axis L and about upper portion 44 of connector portion 40. In one feature of the present invention, each of locking members 26a, 26b has a substantially similar configuration. However, it is also contemplated that locking members 26a, 26b may take on different configurations depending on the particular application. Locking members 26a, 26b are at least partially formed of a shape-memory material such as, for example, Nitinol®.

As is most clearly seen in FIG. 4, locking members 26a, 26b are generally ring-shaped and define an inner diameter $D_6$. It should be understood that while locking members 26a, 26b are depicted as circular rings, other shapes and configurations are also contemplated as would occur to one of ordinary skill in the art. When the shape-memory material is in its martensitic or room temperature state, inner diameter $D_6$ is slightly greater than the outer diameter $D_1$ of upper portion 44 of connector portion 40. In other words, each of locking members 26a, 26b includes an inner surface 80 that generally corresponds to the outer surface of upper portion 44, such that locking members 26a, 26b can be slidably received over upper portion 44 of first and second modules 22a, 22b when the shape-memory material is at a temperature below its transformation temperature range.

Referring collectively to FIGS. 2–4, connecting apparatus 20 is assembled by positioning flanges 42a, 42b of first module 22a adjacent to and overlapping connector portion 40 of second module 22b, and correspondingly positioning flanges 42a, 42b of second module 22b adjacent to and overlapping connector portion 40 of first module 22a. In other words, connector portion 40 of second module 22b is telescopically disposed between flanges 42a, 42b of first module 22a, and connector portion 40 of first module 22a is telescopically disposed between flanges 42a, 42b of second module 22b. Thus, first module 22a and second module 22b are allowed to translate in a telescopic relationship relative to each other generally along longitudinal axis L. In order to provisionally maintain first and second modules 22a, 22b in this telescopic relationship, first module 22a is advanced toward second module 22b until inwardly extending lips 64a, 64b of first module 22a are positioned beyond lower portion 48 of second module 22b, and lips 64a, 64b of second module 22b are correspondingly positioned beyond lower portion 48 of first module 22a. Because the distance between lips 64a and 64b is slightly less than the diameter of lower portion 48, flanges 42a, 42b are outwardly splayed apart while lips 64a, 64b are slid across lower portion 48. When lips 64a, 64b are positioned beyond lower portion 48 and adjacent annular shoulder 62, flanges 42a, 42b are allowed to snap back into their unsplayed configuration. Thus, lips 64a, 64b cooperate with annular shoulder 62 to provisionally maintain first and second modules 22a, 22b in sliding engagement.

In the specific embodiment of connecting apparatus 20 shown in FIGS. 2–4, flanges 42a, 42b of first and second modules 22a, 22b each respectively include lips 64a, 64b. However, it should be understood that lips 64a, 64b are not necessarily required to be included on both pairs of flanges in order to provisionally maintain modules 22a, 22b in sliding engagement. For example, lips 64a, 64b could be included only on flanges 42a, 42b of second module 22b. Similarly, it should also be understood that each of flanges 42a, 42b do not necessarily have to include an inwardly extending lip. For example, flange 42a could include lip 64a, but flange 42b need not necessarily include lip 64b. Additionally, although the specific embodiment of connecting apparatus 20 illustrates each of first and second modules 22a, 22b as including annular shoulder 62, it should be understood that annular shoulder 62 is not necessarily required to be included on both modules 22a and 22b. For example, if an inwardly extending lip is included on either (or both) of flanges 42a, 42b of first module 22a, then annular shoulder 62 must be included on second module 22b, but not necessarily on first module 22a. Moreover, it should be understood that annular shoulder 62 need not necessarily be defined continuously about connector portion 40. For example, annular shoulder 62 could be defined about only a portion of connector portion 40, or could be defined about generally opposing portions of connector portion 40 between flanges 42a, 42b.

In addition to allowing modules 22a, 22b to translate in a telescopic relationship along longitudinal axis L, connecting apparatus 20 also allows modules 22a and 22b to rotate relative to each other generally about axis L. As most clearly illustrated in FIGS. 2–4, flanges 42a, 42b of first module 22a are positioned between flanges 42a, 42b of second module 22b. Thus, flanges 42a, 42b of module 22a and flanges 42a, 42b of module 22b are allowed to freely rotate between one another about axis L. The degree of allowable relative rotation between modules 22a and 22b is dictated by angle $\alpha_1$ and angle $\alpha_2$, as illustrated in FIG. 7. More specifically, the degree of allowable relative rotation between modules 22a and 22b is equal to $\alpha_2-\alpha_1$. In one specific embodiment, angle $\alpha_1$ is about 60° and angle $\alpha_2$ is about 120°. In this specific embodiment, the amount of allowable relative rotation between modules 22a and 22b is about 60°.

Referring again to FIGS. 2–4, compression members 24a, 24b are shown positioned about flanges 42a, 42b of first and second modules 22a, 22b. Compression members 24a, 24b have a first configuration in which their effective inner diameter $D_5$ is slightly larger than the effective outer diameter $D_4$ of flanges 42a, 42b when the shape-memory material within compression members 24a, 24b is in its martensitic state (i.e., at a temperature below the transformation temperature range). Ideally, the shape-memory material will remain in its martensitic state at room temperature or somewhat below room temperature. Thus, while compression members 24a, 24b are maintained in their first configuration, their axial positions along flanges 42a, 42b can be adjusted and first and second modules 22a, 22b are correspondingly allowed to telescopically translate and rotate relative to one another.

Spinal rod 14 is received within opening 52 of first module 22a, and upper portion 32 of bone anchor 16 is received within opening 52 of second module 22b. Bone anchor 16 can then be engaged to a portion of vertebra V by placing a driving tool (not shown) into tool receiving recess 36 and driving threaded shank 30 into vertebral bone. Preferably, bone anchor 16 is driven into vertebra V to a recommended depth for adequate fixation, but preferably not so deep that connecting apparatus 20 will contact or press against vertebral bone when attached to bone anchor 16. It should be understood that bone anchor 16 can alternatively be driven into a portion of vertebra V prior to upper portion 32 being received within opening 52. It should also be understood that spinal rod 14 and bone anchor 16 can respectively be received within opening 52 of first and second modules 22a and 22b prior to the assembly of connecting apparatus 20. In other words, first and second modules 22a and 22b can be assembled after insertion of spinal rod 14 and upper portion 32 of bone anchor 16 within openings 52. It should further be understood that spinal rod 14 can be received within opening 52 of either first module 22a or second module 22b. Bone anchor 16 can then be received within the other of openings 52.

Locking members 26a and 26b are positioned about upper portion 44 of first and second modules 24a, 24b and adjacent annular shoulder 60. Locking members 26a, 26b have a first configuration in which their effective inner diameter $D_6$ is slightly larger than the effective outer diameter $D_1$ of upper portion 44 when the shape-memory material within locking members 26a, 26b is in its martensitic state. Ideally, the shape-memory material will remain in its martensitic state at room temperature or somewhat below room temperature. Thus, while locking members 26a, 26b are maintained in their first configuration, they can be positioned about upper portion 44 of connector portion 40. Spinal rod 14 and bone anchor 16 are correspondingly allowed to slidably translate within opening 52 relative to clamping section 50. In other words, connecting apparatus 20 is allowed to slide along the length of spinal rod 14 and pivot about spinal rod 14. Likewise, connecting apparatus 20 is allowed to slide along the length of upper portion 32 of bone anchor 16 and pivot about upper portion 32.

Once first module 22a is positioned at a desired axial and rotational position relative to second module 22b, compression members 24a, 24b are heated up. As the temperature of compression members 24a, 24b is increased beyond the transformation temperature range of the shape-memory material, the shape-memory material shifts from its martensitic state to its austenitic state. In the austenitic state, compression members 24a, 24b are reformed into a second configuration in which their inner diameter $D_5$ is reduced. Thus, when compression members 24a, 24b are reformed into their second configuration at a temperature above the transformation temperature range of the shape-memory material, compression members 24a, 24b will contract about flange 42a, 42b of first and second modules 22a and 22b. As compression members 24a, 24b engage and tighten about flanges 42a, 42b of modules 22a, 22b, each pair of flanges 42a, 42b will correspondingly compress tightly against connector portion 40, and more specifically lower portion 48. The super elastic properties of the shape-memory material enables significant recoverable strains, and therefore compression forces, to be developed by compression members 24a, 24b. These forces are transmitted to flanges 42a, 42b, which in turn tightly engage lower portion 48 of connector portion 40, thereby limiting movement of first module 22a relative to second modules 22b. Thus, after compression members 24a, 24b are reformed into their second configuration, first module 22a and second module 22b will no longer be allowed to freely translate along axis L and freely rotate about axis L relative to one another.

Although there are various ways in which to increase the temperature of the shape-memory material above its transformation temperature range, in one specific embodiment of the present invention, when connecting apparatus 20, and more specifically compression members 24a, 24b, are placed within a patient, the body temperature of the patient will increase the temperature of the shape-memory material and cause it to move from its martensitic state to its austenitic state. However, it should be understood that the temperature of the shape-memory material may be increased above its transformation temperature range by running electric current through compression members 24a, 24b and increasing their temperature through resistance heating. Alternatively, the temperature of compression members 24a, 24b may be increased by way of magnetic induction, the application of which would be apparent to one of ordinary skill in the art.

Once connector apparatus 20 is positioned at a desired axial location along spinal rod 14 and pivoted to a desired angular alignment about spinal rod 14, locking member 25a is heated up. Likewise, once connector apparatus 20 is positioned at a desired axial location along upper portion 32 of bone anchor 16 and pivoted to a desired angular alignment about upper portion 32, locking member 26b is heated up. Preferably, locking members 26a and 26b are heated up substantially concurrently. Ideally, locking members 26a and 26b are heated up substantially concurrently with compression members 24a, 24b. It should be understood that locking members 26a, 26b preferably, but not necessarily, are made of a shape-memory material having the same transformation temperature range as that of compression members 24a, 24b. As the temperature of locking members 26a, 26b is increased beyond the transformation temperature range of the shape-memory material, the shape-memory material shifts from its martensitic state to its austenitic state. In the austenitic state, locking members 26a, 26b are reformed into a second configuration in which their inner diameter $D_6$ is reduced to a preprogrammed size slightly smaller than outer diameter $D_1$ of upper portion 44. Thus, when locking members 26a, 26b are reformed into their second configuration at a temperature above the transformation temperature range of the shape-memory material, locking members 26a, 26b will contract about upper portion 44 of first and second modules 22a, 22b, respectively. As locking members 26a, 26b engage and tighten about upper portion 44 of modules 22a, 22b, sidewalls 58a, 58b will correspondingly compress tightly against spinal rod 14 and bone anchor 16. Significant compression forces are developed by locking members 26a, 26b. These forces are transmitted to clamping section 50 of modules 22a and 22b, which in turn tightly engage spinal rod 14 and bone anchor 16, thereby limiting movement of first module 22a relative to spinal rod 14 and second module 22b relative to bone anchor 16. Thus, connecting apparatus 20 will no longer be allowed to freely slide along the length or pivot about spinal rod 14 and upper portion 32 of bone anchor 16. In one embodiment of the present invention, when connecting apparatus 20, and more specifically locking members 26a, 26b, are placed within a patient, the body temperature of the patient will increase the temperature of the shape-memory material and cause it to move from its martensitic state to its austenitic state.

Clamping section 50 of first module 22a is configured to allow spinal rod 14 to bend within opening 52. As is most clearly shown in FIG. 6, second cross-sectional area 52b has a diameter somewhat larger than first cross-sectional area 52a. In turn, first cross-sectional area 52a has a diameter that is substantially equal to the diameter of spinal rod 14. If spinal rod 14 is required to be bent to more closely conform to the curvature of the spinal column, second cross-sectional area 52b provides sufficient space for spinal rod 14 to deform and bend within opening 52. It should be understood that second cross-sectional area 52b is not necessarily required to be included in clamping section 50 of second module 22b unless upper portion 32 of bone anchor 16 is also required to bend within opening 52.

In an alternative embodiment of clamping section 50 of first and second modules 22a, 22b, slit 56 is widened to approximately the width of first cross-sectional area 52a of opening 52. Thus, clamping section 50 may define an open, U-shaped recess. In this embodiment, spinal rod 14 and upper portion 32 of bone anchor 16 could be top-loaded into clamping section 50 of modules 22a, 22b. Side walls 58a, 58b would thus form a pair of gripping prongs which, when heated to a temperature above the transformation temperature range of the shape-memory material, would contract about a portion of spinal rod 14 or upper portion 32 of bone anchor 16. Relative movement between connecting apparatus 20 and spinal rod 14 and bone anchor 16 would thus be limited.

In an alternative embodiment of connecting apparatus 20, connector portion 40 of first and second modules 22a, 22b could define a circular groove positioned generally about longitudinal axis L and sized to receive flanges 42a, 42b of the opposing module therein. Instead of positioning compression members 24a, 24b around flanges 42a, 42b of modules 22a, 22b, compression members 24a, 24b could alternatively be positioned between flanges 42a, 42b of modules 22a, 22b. In this alternative embodiment, compression members 24a, 24b would have a first configuration in which their outer diameter would be sized slightly smaller than inner diameter $D_3$ of flanges 42a, 42b when the shape-memory material is in its martensitic state. Thus, while compression members 24a, 24b are maintained in this first configuration, first and second modules 22a, 22b would be allowed to telescopically translate and rotate relative to one another. Once first module 22a is positioned at a desired axial and rotational position relative to second module 22b, compression members 24a, 24b may be heated up. As the temperature increases beyond the transformation temperature range of the shape-memory material, the shape-memory material will shift from its martensitic state to its austenitic state. In the austenitic state, compression members 24a, 24b will be reformed into a second configuration in which their outer diameter is increased to a preprogrammed size slightly larger than inner diameter $D_3$ of flanges 42a, 42b. Thus, when compression members 24a, 24b are reformed into their second configuration at a temperature above the transformation temperature range of the shape-memory material, compression members 24a, 24b will expand and press tightly against inner surfaces 63a, 63b of flanges 42a, 42b. Flanges 42a, 42b will correspondingly compress tightly against the outer surface of the circular groove defined in connector portion 40 of the opposing module. Thus, first module 22a and second module 22b will no longer be allowed to freely translate along axis L and freely rotate about axis L relative to one another. In this alternative embodiment, connecting apparatus 20 could also be configured to provisionally maintain first and second modules 22a, 22b in a telescopic relationship, similar to the telescopic relationship described above. However, lips 64a, 64b must correspondingly be repositioned to extend outwardly from flanges 42a, 42b. Similarly, annular shoulder 62 must be defined by the outer surface of the circular groove defined in connector portion 40.

To better illustrate the construction of connecting apparatus 20, the dimensions of one manufactured embodiment are hereafter listed. It should be understood, however, that these dimensions are exemplary and are not intended to limit the scope of protection sought. The use of dimensions and tolerances other than those listed are contemplated as within the scope of the invention. For simplicity, reference will only be made to first module 22a. However, it is understood that first and second modules 22a, 22b may have substantially identical configurations or may have different configurations.

Referring to FIGS. 5–7, first module 22a defines a longitudinal axis L about which it is generally symmetrical. Connector portion 40 has an overall height of about 10 mm measured from the top surface of upper portion 44 to the bottom surface of lower portion 48. More specifically, upper portion 44 has a height of about 2.023 mm, intermediate portion 46 has a height of about 5.477 mm and lower portion 48 has a height of about 2.5 mm. Diameter $D_1$ of upper portion 44 is preferably about 9 mm and diameter $D_2$ of lower portion 48 is preferably about 14 mm. Intermediate portion 46 has a diameter slightly less than diameter $D_2$ of lower portion 48, and is preferably about 13 mm. As described above, flanges 42a, 42b extend across an angle $\alpha_1$.

Preferably, angle $\alpha_1$ is about 60°. As also described above, flanges 42a, 42b are separated from one another by angle $\alpha_2$. Preferably, angle $\alpha_2$ is about 120°. Inner diameter $D_3$, as measured between inner surfaces 63a, 63b, is substantially equal to outer diameter $D_2$ of lower portion 48. More specifically, diameter $D_3$ is preferably about 14 mm. Outer diameter $D_4$, as measured between outer surfaces 65a, 65b, is preferably about 16 mm. Therefore, the thickness of each of flanges 42a, 42b is approximately 1 mm. Inwardly extending lips 64a, 64b are preferably rounded to a radius of 0.5 mm. Correspondingly, annular shoulder 62 preferably defines a rounded fillet of about 0.5 mm. The overall length of module 22a, as measured between the upper surface of upper portion 44 and the lower end of flanges 42a, 42b, is about 20 mm. The center line of opening 52, including first cross-sectional area 52a and second cross sectional area 52b, is located about 4.74 mm from the bottom surface of lower portion 48. First cross-sectional area 52a preferably has a diameter of about 6.477 mm and second cross-sectional area 52b preferably has a diameter of about 6.985 mm. Second cross-sectional area 52b is generally centered along axis L and has an overall length of about 8 mm.

Referring to FIG. 3, compression members 24a, 24b have an inner diameter $D_5$ when at a temperature below the transformation temperature range (i.e., when the shape-memory material is in its martensitic state). In this state, inner diameter $D_5$ is slightly greater than outer diameter $D_4$ of flanges 42a, 42b, and is preferably about 16.5 mm. When compression members 24a, 24b are increased to a temperature above the transformation temperature range (i.e., when the shape-memory material is in its austenitic state), inner diameter $D_5$ is reduced so that inner surface 70 may bear against flanges 42a, 42b and tightly compress flanges 42a, 42b against connector portion 40 of the opposing module. The outer diameter of compression members 24a, 24b is preferably about 18 mm. The thickness of compression members 24a, 24b is preferably about 3 mm.

Locking members 26a, 26b have an inner diameter $D_6$ when at a temperature below the transformation temperature range. In this state, inner diameter $D_6$ is slightly greater than outer diameter $D_1$ of upper portion 44 of connector portion 40, and is preferably about 9.5 mm. When locking members 26a, 26b are increased to a temperature above the transformation temperature range, inner diameter $D_6$ is reduced so that inner surface 80 may bear against upper portion 44 and tightly compress sidewalls 58a, 58b against the corresponding spinal rod 14 or bone anchor 16. The outer diameter of locking members 26a, 26b is preferably equal to or slightly less than the diameter of intermediate portion 46, and is preferably about 13 mm. The thickness of locking members 26a, 26b is preferably slightly less than or equal to the height of upper portion 44 and is preferably about 2 mm. As previously mentioned, variations in these design parameters which would occur to a person of ordinary skill in the art are contemplated as within the scope of the invention and are therefore not intended to limit the scope of protection.

In an alternative embodiment of the present invention, system 100 is provided as shown in FIGS. 8–10. In this embodiment, bone anchor 16 is connected to spinal rod 14 by way of connecting apparatus 20'. Connecting apparatus 20' includes first and second modules 22a', 22b'. However, unlike connecting apparatus 20, connecting apparatus 20' does not include compression members 24a, 24b or locking members 26a, 26b. First and second modules 22a' and 22b' are configured dimensionally identical to first and second modules 22a, 22b. Therefore, reference will be made to like structural elements previously labeled in FIGS. 5–7 and discussed in detail above. It should be understood, however, that first and second modules 22a', 22b' may take on configurations different from those of modules 22a, 22b.

First and second modules 22a', 22b' are shown assembled substantially identical to first and second modules 22a, 22b, as illustrated in FIG. 2 and discussed in detail above. Specifically, connecting apparatus 20' is assembled by positioning flanges 42a, 42b of first module 22a' adjacent to and overlapping connector portion 40 of second module 22b', and correspondingly positioning flanges 42a, 42b of second module 22b' adjacent to and overlapping connector portion 40 of first module 22a'. Thus, similar to modules 22a and 22b, modules 22a' and 22b' are allowed to translate in a telescopic relationship relative to one another generally along longitudinal axis L, and are provisionally maintained in this telescopic relationship by way of cooperation between lips 64a, 64b and annular shoulder 62. Likewise, modules 22a' and 22b' are allowed to rotate relative to each other generally about axis L.

Rather than using compression members 24a, 24b to limit movement of first module 22a' relative to second module and 22b', a portion of each pair of flanges 42a, 42b is formed of a shape-memory material. More specifically, at least one of flanges 42a, 42b is at least partially formed of a shape-memory material such as, for example, Nitinol®.

Referring now to FIG. 9, therein is illustrated a first operational configuration of connecting apparatus 20'. Flanges 42a, 42b of first and second modules 24a', 24b' have a first configuration in which inner diameter $D_3$ is substantially equal to outer diameter $D_2$ of lower portion 48 when the shape-memory material is in its martensitic state (i.e., at a temperature below the transformation temperature range). It should be understood that, for illustration purposes, FIG. 9 depicts an exaggerated degree of clearance between flanges 42a, 42b and lower portion 48. Ideally, the shape-memory material will remain in its martensitic state at room temperature or somewhat below room temperature. Thus, while flanges 42a, 42b are maintained in their first configuration, first and second modules 22a' and 22b' are allowed to telescopically translate along axis L and rotate about axis L relative to one another.

Referring to FIG. 10, there is illustrated a second operational configuration of connecting apparatus 20'. Once first and second modules 22a', 22b' are positioned at a desired axial and rotational position relative to one another, each pair of flanges 42a, 42b is heated up. As the temperature increases beyond the transformation temperature range of the shape-memory material, the shape-memory material shifts from its martensitic state to its austenitic state. In the austenitic state, each pair of flanges 42a, 42b is reformed into a second configuration in which inner diameter $D_3$ is reduced. Thus, when flanges 42a, 42b is reformed into their second configuration at a temperature above the transformation temperature range of the shape-memory material, flanges 42a, 42b will contract about lower portion 48 of the opposing module. In this second configuration, flanges 42a, 42b are compressed tightly against lower portion 48 of connector portion 40, thereby limiting movement of first module 22a' relative to second module 22b'. Accordingly, first and second modules 22a', 22b' will no longer be allowed to freely translate along axis L and freely rotate about axis L relative to one another.

Similar to connecting apparatus 20, connecting apparatus 20' can have an alternative embodiment in which connector portion 40 of first and second modules 22a', 22b' defines a circular groove positioned generally about axis L and sized to receive flanges 42a, 42b of the opposing module therein. Flanges 42a, 42b of first and second modules 24a', 24b' have a first configuration in which outer diameter $D_4$ would be sized slightly smaller than the outer diameter of the circular groove defined in connector portion 40 of the opposing module when the shape-memory material is in its martensitic state. While in this first configuration, first and second modules 22a', 22b' would be allowed to telescopically translate and rotate relative to one another. As the temperature increases beyond the transformation temperature range of the shape-memory material, the shape-memory material will move from its martensitic state to its austenitic state. In the austenitic state, each pair of flanges 42a, 42b would be reformed into a second configuration in which outer diameter $D_4$ is increased. Thus, when flanges 42a, 42b are reformed into their second configuration, they will expand out and compress tightly against the outer surface of the circular groove defined in connector portion 40 of the opposing module. Thereafter, first module 22a' and second module 22b' will no longer be allowed to freely translate along axis L and freely rotate about axis L relative to one another. In this alternative embodiment, lips 64a, 64b must be repositioned to extend outwardly from flanges 42a, 42b and annular shoulder 62 must he defined by the outer surface of the circular groove defined in connector portion 40.

Referring back to FIG. 8, rather than using locking member 26a to limit movement of first module 22a' relative to spinal rod 14, and locking member 26b to limit movement of second module 22b' relative to bone anchor 16, a portion of each of clamping sections 50 is at least partially formed of a shape-memory material. More specifically, at least one of sidewalls 58a, 58b is at least partially formed of a shape-memory material such as, for example Nitinol®.

Referring again to FIG. 9, the first operational configuration of connecting apparatus 20' shows clamping section 50 of first and second modules 22a', 22b' as having a first configuration. This first configuration illustrates opening 52 as having a diameter, which is slightly greater than the outer diameter of spinal rod 14 and upper portion 32 of bone anchor 16 when the shape-memory material is in its martensitic state. Thus, while clamping section 50 is maintained in this first configuration, first module 22a' is allowed to slide along the length and pivot about spinal rod 14. Correspondingly, second module 22b' is allowed to slide along the length and pivot about upper portion 32 of bone anchor 16.

Referring again to FIG. 10, once first and second modules 22a', 22b' are respectively positioned at a desired axial and pivotal position relative to spinal rod 14 and bone anchor 16, clamping section 50 of modules 22a', 22b' is heated up. As the temperature of clamping section 50 is increased beyond the transformation temperature range of the shape-memory material, the shape-memory material shifts from its martensitic state to its austenitic state. In the austenitic state, clamping section 50 is reformed into a second configuration in which the diameter of opening 52, and more specifically cross-sectional area 52a, is reduced. Thus, when clamping section 50 of modules 22a', 22b' is reformed into its second configuration, it will respectively contract about spinal rod 14, and upper portion 32 of bone anchor 16. In this second configuration, sidewalls 58a, 58b compress tightly against spinal rod 14 and upper portion 32 of bone anchor 16, thereby limiting movement of first module 22a' relative to spinal rod 14 and second module 22b' relative to bone anchor 16. Accordingly, first and second modules 22a', 22b' will no longer be allowed to freely slide along the length or pivot about spinal rod 14 or upper portion 32 of bone anchor 16.

In an alternative embodiment of clamping section 50 of first and second modules 22a', 22b', slit 56 is widened to approximately the width of first cross-sectional area 52a of opening 52. Thus, clamping section 50 would define an open, U-shaped recess. In this embodiment, spinal rod 14 and upper portion 32 of bone anchor 16 could be top-loaded into clamping section 50 of modules 22a', 22b'. Side walls 58a, 58b would thus form a pair of gripping prongs which, when heated to a temperature above the transformation temperature range of the shape-memory material, would contract about a portion of spinal rod 14 or upper portion 32 of bone anchor 16. Relative movement between connecting apparatus 20' and spinal rod 14 and bone anchor 16 would thus be limited.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

For example, while the preferred embodiments of system 10 and system 100 contemplate connecting spinal rod 14 to bone anchor 16, connecting apparatus 20 and connecting apparatus 20' can alternatively be used to connect other members having various configurations. For instance, connecting apparatus 20, 20' could be used to connect spinal rod 14 to a transverse rod, which in turn may be connected to another spinal rod 14 positioned on the opposite side of spinal column 12. Additionally, while the preferred embodiments contemplate connecting a spinal rod to a bone anchor, such as bone anchor 16, other bone engaging fasteners are also contemplated. For instance, connecting apparatus 20, 20' could be used to connect a spinal rod to a vertebral hook or bone bolt. Further, the components of systems 10, 100 can be correspondingly sized according to the portion of a spine within which the particular assembly is to be used. For instance, treatment of the lumbar region of the spine may require components which are sized somewhat larger than components used to treat the thoracic and cervical regions of the spine. Additionally, while connecting apparatus 20 and connecting apparatus 20' have been illustrated and described as having separate and distinct configurations, it should be understood that various aspects and features of either configuration can be combined to form other alternative configurations as well.

What is claimed is:

1. A connecting apparatus, comprising:

a first module having a first connector portion and at least one flange extending therefrom, said first connector portion being adapted for connection to a first member;

a second module having a second connector portion and at least one flange extending therefrom, said second connector portion being adapted for connection to a second member;

said at least one flange of said first module being disposed adjacent to and overlapping a portion of said second connector portion, said at least one flange of said second module being disposed adjacent to and overlapping a portion of said first connector portion; and shape-memory means cooperating with said at least one flange of said first and second modules for allowing movement of said first module relative to said second module when at one temperature, and limiting movement of said first module relative to said second module when at a different temperature.

2. The apparatus of claim 1, further comprising means for provisionally maintaining said first and second modules in a telescopic relationship.

3. The apparatus of claim 1, further comprising connector means associated with at least one of said first and second members, said connector means composed of a shape-memory material, said connector means allowing movement of the apparatus relative to said at least one of said first and second members when at one temperature, said connector means limiting movement of the apparatus relative to said at least one of said first and second members when at a different temperature.

4. A connecting apparatus, comprising:
a first module having a first connector portion and a first flange extending therefrom, said first connector portion being adapted for connection to a first member;
a second module having a second connector portion and a second flange extending therefrom, said second connector portion being adapted for connection to a second member;
said first flange being disposed adjacent to and overlapping a portion of said second connector portion, said second flange being disposed adjacent to and overlapping a portion of said first connector portion;
a first compression member at least partially formed of a shape-memory material, said first compression member being disposed adjacent to said first and second flanges; and
said first compression member having a first configuration at one temperature and a second configuration at a different temperature, said first configuration allowing movement of said first module relative to said second module, said second configuration limiting movement of said first module relative to said second module.

5. The apparatus of claim 4, wherein said first compression member is disposed about at least a portion of both said first and second flanges and engages said first and second flanges and compresses said first and second flanges respectively against said second and first connector portions when said first compression member is in said second configuration.

6. The apparatus of claim 4, wherein said first module has a third flange extending therefrom at a location generally opposite said first flange, said first and third flanges defining a first pair of flanges, said second module has a fourth flange extending therefrom at a location generally opposite said second flange, said second and fourth flanges defining a second pair of flanges.

7. The apparatus of claim 6, wherein said first connector portion is telescopically disposed between said flanges of said second pair, said second connector portion being telescopically disposed between said flanges of said first pair, and wherein said first and second modules are allowed to translate in a telescopic relationship relative to each other when said first compression member is in said first configuration.

8. The apparatus of claim 7, wherein at least one flange of said first and second pairs of flanges defines an inwardly extending lip, and wherein at least one of said first and second connector portions disposed between the flanges of said at least one of said first and second pairs of flanges has an outer surface defining a shoulder, said lip cooperating with said shoulder to provisionally maintain said first and second modules in said telescopic relationship.

9. The apparatus of claim 8, wherein both flanges of said at least one of said first and second pairs of flanges define said lip, and wherein said shoulder is defined continuously about said outer surface.

10. The apparatus of claim 6, wherein the flanges of said first pair are disposed between the flanges of said second pair, and wherein said first and second modules are allowed to rotate relative to each other when said first compression member is in said first configuration.

11. The apparatus of claim 4, wherein said first compression member is a ring defining an inner annular surface, said first and second flanges each defining a rounded outer surface generally corresponding to said inner annular surface.

12. The apparatus of claim 4, further comprising a second compression member at least partially formed of said shape-memory material, said second compression member being disposed about at least a portion of both said first and second flanges.

13. The apparatus of claim 4, further comprising a locking member at least partially formed of a shape-memory material, and wherein at least one of said first and second connector portions includes a clamping section associated with one of said first and second members, said locking member being disposed about at least a portion of said clamping section, said locking member allowing movement of said clamping section relative to said one of said first and second members when at one temperature of said locking member, said locking member contracting about said clamping section when at a different temperature of said locking member to limit movement of said clamping section relative to said one of said first and second members.

14. The apparatus of claim 13, wherein said locking member is a ring defining an inner annular surface, said clamping section defining a rounded outer surface generally corresponding to said inner annular surface.

15. The apparatus of claim 13, wherein said shape-memory material of the first compression member and said shape-memory material of the locking member have the same composition.

16. The apparatus of claim 13, wherein said clamping section defines an opening extending therethrough.

17. The apparatus of claim 16, wherein said clamping section further defines a slit intersecting said opening.

18. The apparatus of claim 16, wherein said opening is sized to receive a rod, said clamping section configured to allow said rod to bend within said opening.

19. The apparatus of claim 4, wherein said first member is a spinal rod and said second member is a bone anchor.

20. The apparatus of claim 4, further comprising first and second locking members, each of said first and second locking members being at least partially formed of a shape-memory material; and
wherein said first member comprises a first part of a spinal column, and said second member comprises a second part of said spinal column; and
wherein said first connector portion includes a first clamping section defining a first opening extending therethrough, said first opening being sized to receive a spinal rod configured to connect to said first part of said spinal column, said first locking member being disposed about at least a portion of said first clamping section, said first locking member allowing movement of said first clamping section relative to said spinal rod when at one temperature, said first locking member contracting about said first clamping section when at a different temperature to limit movement of said first clamping section relative to said spinal rod; and
wherein said second connector portion includes a second clamping section defining a second opening extending therethrough, said second opening being sized to receive a bone anchor configured to engage said second part of said spinal column, said second locking member being disposed about at least a portion of said second clamping section, said second locking member allowing movement of said second clamping section relative to said bone anchor when at one temperature, said second locking member contracting about said second clamping section when at a different temperature to limit movement of said second clamping section relative to said bone anchor.

21. A connecting apparatus, comprising:

a first module having a first connector portion and a first pair of flanges extending therefrom, said first connector portion being adapted for connection to a first member;

a second module having a second connector portion and a second pair of flanges extending therefrom, said second connector portion being adapted for connection to a second member;

at least one flange of said first pair of flanges being at least partially formed of a shape-memory material, said first pair of flanges being disposed adjacent to and overlapping a portion of said second connector portion;

at least one flange of said second pair of flanges at least partially formed of a shape-memory material, said second pair of flanges being disposed adjacent to and overlapping a portion of said first connector portion; and said first and second pairs of flanges having a first configuration at one temperature and a second configuration at a different temperature, said first configuration allowing movement of said first module relative to said second module, said second configuration limiting movement of said first module relative to said second module.

22. The apparatus of claim 21, wherein said first and second pairs of flanges compress respectively against said second and first connector portions when said first and second pairs of flanges are in said second configuration.

23. The apparatus of claim 21, wherein at least one flange of said first and second pairs of flanges defines an inwardly extending lip, and wherein at least one of said first and second connector portions disposed between the flanges of said at least one of said first and second pairs of flanges has an outer surface defining a shoulder, said lip cooperating with said shoulder to provisionally maintain said first and second modules in a telescopic relationship.

24. The apparatus of claim 23, wherein both flanges of said at least one of said first and second pairs of flanges define said lip, and wherein said shoulder is defined continuously about said outer surface.

25. The apparatus of claim 21, wherein the flanges of said first pair are disposed between the flanges of said second pair, and wherein said first and second modules are allowed to rotate relative to each other when said first and second pairs of flanges are in said first configuration.

26. The apparatus of claim 21, wherein at least one of said first and second connector portions includes a clamping section associated with one of said first and second members, said clamping section at least partially formed of a shape-memory material, said clamping section allowing movement of said clamping section relative to said one of said first and second members when at one temperature, said clamping section inwardly contracting when at a different temperature to limit movement of said clamping section relative to said one of said first and second members.

27. The apparatus of claim 26, wherein said shape-memory material of the flanges and said shape-memory material of the clamping section have the same composition.

28. The apparatus of claim 26, wherein said clamping section defines an opening extending therethrough.

29. The apparatus of claim 28, wherein said clamping section includes a pair of generally opposing side walls, said side walls defining said opening, said opening being a C-shaped recess.

30. The apparatus of claim 28, wherein said first member comprises a first part of a spinal column and said second member comprises a second part of said spinal column, and wherein said connecting apparatus is part of a spinal fixation system, said first connector portion including a first of said clamping section, said opening in said first clamping section being sized to receive a spinal rod, said spinal rod being configured to connect to said first part of said spinal column, said second connector portion including a second of said clamping section, said opening in said second clamping section being sized to receive a bone anchor, said bone anchor being configured to engage said second part of said spinal column.

31. The apparatus of claim 21, wherein said first member is a spinal rod and said second member is a bone anchor.

32. A connecting apparatus, comprising:

a first module having a first connector portion, said first connector portion being adapted for connection to a first member;

a second module having a second connector portion and a pair of flanges extending therefrom, said pair of flanges positioned about an axis, said second connector portion being adapted for connection to a second member, said pair of flanges being disposed adjacent to and overlapping a portion of said first connector portion;

a compression member at least partially formed of a shape-memory material, said compression member being positioned along said axis and disposed about at least a portion of said pair of flanges, said compression member having a first configuration at one temperature and a second configuration at a different temperature, said first configuration allowing movement of said first module relative to said second module, said second configuration limiting movement of said first module relative to said second module; and a locking member at least partially formed of a shape-memory material, and wherein at least one of said first and second connector portions includes a clamping section associated with one of said first and second members, said locking member being positioned along said axis and disposed about at least a portion of said clamping section, said locking member allowing movement of said clamping section relative to said one of said first and second members when at one temperature of said locking member, said locking member contracting about said clamping section when at a different temperature of said locking member to limit movement of said clamping section relative to said one of said first and second members.

33. The apparatus of claim 32, wherein at least one flange of said pair of flanges defines an inwardly extending lip, and wherein said second connector portion has an outer surface defining a shoulder, said lip cooperating with said shoulder to provisionally maintain said first and second modules in a telescopic relationship.

34. The apparatus of claim 32, wherein said clamping section defines an opening extending therethrough, said opening sized to receive a rod, said clamping section configured to allow said rod to bend within said opening.

35. A connecting apparatus, comprising:

a first module having a first connector portion, said first connector portion being adapted for connection to a first member;

a second module having a second connector portion and a pair of flanges extending therefrom, said second connector portion being adapted for connection to a second member;

at least one flange of said pair of flanges being at least partially formed of a shape-memory material, said pair of flanges being disposed adjacent to and overlapping a portion of said first connector portion;

said pair of flanges having a first configuration at one temperature and a different configuration at a second temperature, said first configuration allowing movement of said first module relative to said second module, said second configuration limiting movement of said first module relative to said second module; and wherein at least one of said first and second connector portions includes a clamping section associated with one of said first and second members, said clamping section at least partially formed of a shape-memory material, said clamping section allowing movement of said clamping section relative to said one of said first and second members at one temperature, said clamping section inwardly contracting at a different temperature to limit movement of said clamping section relative to said corresponding one of said first and second members.

36. The apparatus of claim 35, wherein at least one flange of said pair of flanges defines an inwardly extending lip, and wherein said second connector portion has an outer surface defining a shoulder, said lip cooperating with said shoulder to provisionally maintain said first and second modules in a telescopic relationship.

* * * * *